United States Patent [19]

Brody

[11] Patent Number: 4,547,243
[45] Date of Patent: Oct. 15, 1985

[54] METHOD AND APPARATUS FOR CONTINUOUSLY ATTACHING ELASTIC STRANDS TO DISPOSABLE ABSORBENT PRODUCTS

[75] Inventor: David L. Brody, Edison, N.J.

[73] Assignee: Whitestone Products, Piscataway, N.J.

[21] Appl. No.: 658,836

[22] Filed: Oct. 9, 1984

[51] Int. Cl.⁴ ............................................. B32B 31/06
[52] U.S. Cl. .................................. 156/164; 156/229; 156/291; 156/494; 156/522; 156/548; 604/385 A
[58] Field of Search ............... 156/164, 229, 494, 495, 156/291, 548, 522; 604/385 R, 385 A

[56] References Cited

U.S. PATENT DOCUMENTS

| | | | |
|---|---|---|---|
| 3,544,405 | 12/1970 | Nakai et al. | 156/164 |
| 3,578,155 | 5/1971 | Small | 206/58 |
| 3,599,293 | 8/1971 | Nystrand | 19/155 |
| 3,860,003 | 1/1975 | Buell | 604/389 |
| 4,050,462 | 9/1977 | Woon et al. | 604/389 |
| 4,081,301 | 3/1978 | Buell | 156/164 |
| 4,227,952 | 10/1980 | Sabee | 156/164 |
| 4,239,578 | 12/1980 | Gore | 156/361 |
| 4,240,866 | 12/1980 | Rega | 156/496 |
| 4,261,782 | 4/1981 | Teed | 156/361 |
| 4,284,454 | 8/1981 | Joa | 156/303 X |
| 4,285,747 | 8/1981 | Rega | 156/164 |
| 4,293,367 | 10/1981 | Klasek et al. | 156/494 |
| 4,297,157 | 10/1981 | Van Vliet | 156/164 |
| 4,300,967 | 11/1981 | Sigl | 156/164 |
| 4,333,782 | 6/1982 | Pieniak | 156/164 |
| 4,353,762 | 10/1982 | Bouda | 156/164 |
| 4,364,787 | 12/1982 | Radzins | 156/164 |
| 4,379,016 | 4/1983 | Stemmler | 156/205 |
| 4,385,224 | 5/1983 | Kaufman et al. | 156/495 X |
| 4,388,075 | 6/1983 | Mesek et al. | 604/385 |
| 4,397,704 | 8/1983 | Frick | 156/201 |
| 4,405,397 | 9/1983 | Teed | 156/164 |
| 4,412,881 | 11/1983 | Sigl | 156/164 |
| 4,417,935 | 11/1983 | Spencer | 156/164 X |

FOREIGN PATENT DOCUMENTS 2244591 3/1974 Fed. Rep. of Germany .

Primary Examiner—David Simmons
Attorney, Agent, or Firm—Francis J. Bouda

[57] ABSTRACT

A continuous elastic ribbon is fed to a diaper assembly station in a stretched condition while, at the same time, an adhesive is continuously applied to the elastic ribbon. Simultaneously, absorbent batts, as well as webs of moisture-impervious batt sheet material and moisture-impervious top-sheet material are fed to the diaper assembly station. Further, and simultaneously, while the webs are traveling to the assembly station, the quantity of the adhesive applied to the elastic ribbon is changed so that there is substantially less adhesive in pre-determined isolated portions of the stretched elastic ribbon. At the assembly station, a stretched elastic ribbon is adhered to the moisture-impervious backsheet web along portions of the elastic ribbon which intervene the selected areas of the web while lesser quantities of the adhesive are located. After the adhesive is set up, the stretched elastic ribbon adheres to the moisture-impervious backsheet in the pre-selected areas with a force which exceeds the contracting force in the elastic ribbon, whereas in the portions which intervene the selected areas, the force which binds the elastic ribbon to the moisture-impervious backsheet is substantially less than the contracting force of the elastic whereupon the portions of the elastic intervening the selected areas are released from the moisture-impervious backsheet so that the contractible force of elastic becomes ineffective without effecting the functionality of those portions of the elastic adhered to the moisture-impervious backsheet in the selected areas.

7 Claims, 7 Drawing Figures

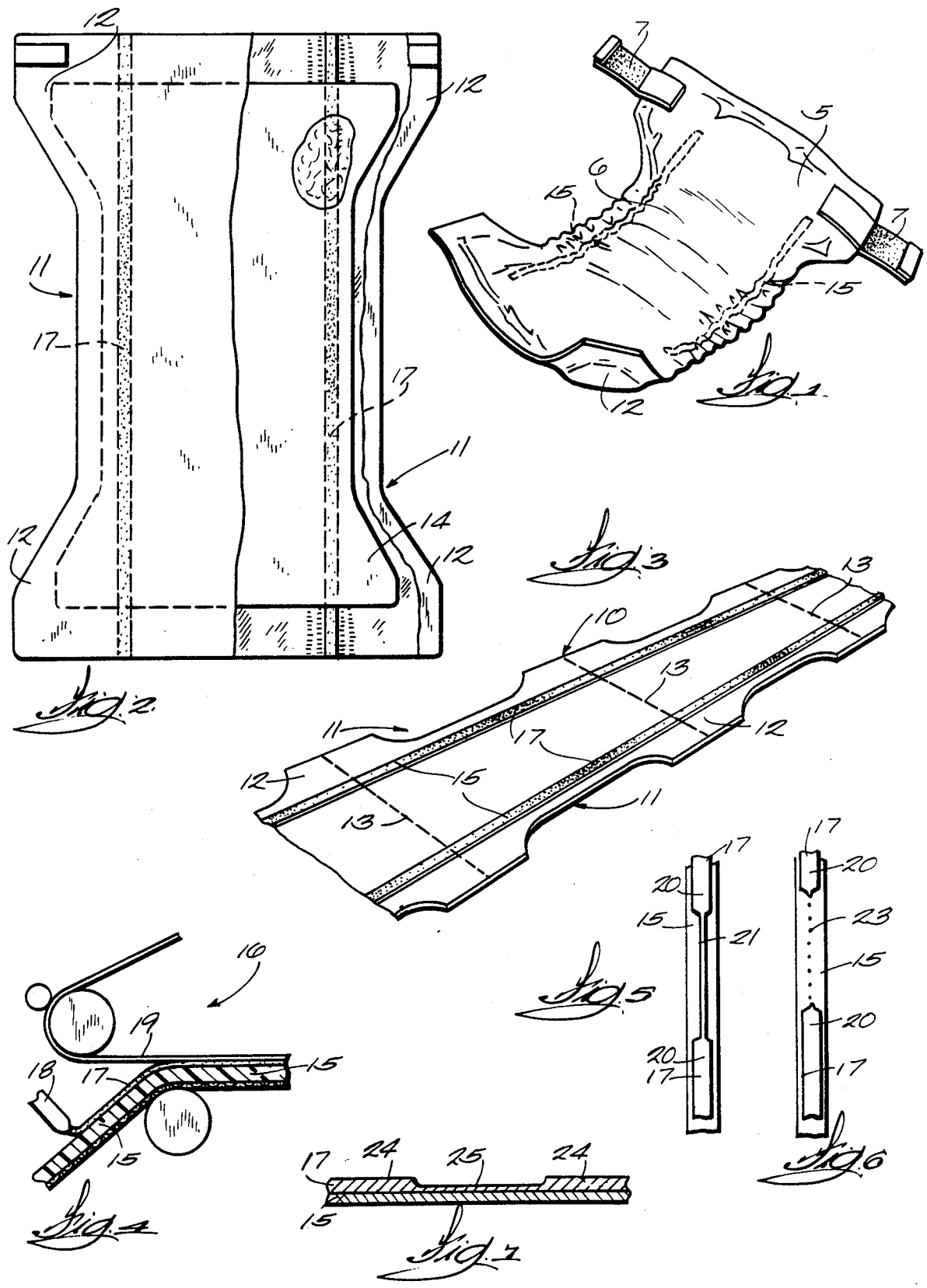

METHOD AND APPARATUS FOR CONTINUOUSLY ATTACHING ELASTIC STRANDS TO DISPOSABLE ABSORBENT PRODUCTS

BACKGROUND OF THE INVENTION

Many past inventions have taught how to secure an elastic ribbon in a stretched condition to continuously move webs of material used in garment manufacture as, for instance, to apply an elasticized waistband to underwear, pantyhose, blouses, pants, and the like. Originally this was done by sewing or by adhesively securing the stretched elastic band in one form or another of the garment.

More recently, the use of such a stretched, elastic band for securing a disposable baby diaper securely in place around the legs of the baby has been shown in issued patents.

U.S. Pat. No. 3,860,003 which issued to Buell on Jan. 14, 1975 shows one form of such "Contractible Side Portions For Disposable Diaper".

Additionally, U.S. Pat. No. 4,081,301, which issued to Buell on Mar. 28, 1978, teaches the "Method And Apparatus For Continuously Attached Discreet, Stretched Elastic Strands To Predetermine Isolated Portions Of Disposable Absorbent Products".

Other recent patents of significance in this field are:

| U.S. Pat. No. | | | |
|---|---|---|---|
| | 4,450,026 | 84-05-22 | Pieniak |
| | 4,447,240 | 84-05-08 | Utsunomiya |
| | 4,437,860 | 84-03-20 | Sigl |
| | 4,432,823 | 84-02-21 | Moore |
| | 4,425,173 | 84-01-10 | Frick |
| | 4,423,823 | 84-02-21 | Moore |
| | 4,407,284 | 83-10-04 | Pieniak |
| | 4,402,690 | 83-09-06 | Redfern |
| | 4,402,688 | 81-10-27 | Julemont |
| | 4,388,075 | 83-06-14 | Mesek |
| | 4,381,781 | 83-05-03 | Sciaraffa |
| | 4,364,787 | 82-12-21 | Radzins |
| | 4,360,398 | 82-11-23 | Sabee |
| | 4,338,938 | 82-07-13 | Seavitt |
| | 4,337,771 | 82-07-06 | Pieniak |
| | 4,336,803 | 82-06-29 | Repke |
| | 4,333,782 | 82-06-08 | Pieniak |
| | 4,326,528 | 82-04-27 | Ryan |
| | 4,324,245 | 82-04-13 | Mesek |
| | 4,300,562 | 81-11-17 | Pieniak |
| | 4,240,866 | 80-12-23 | Rega |

The prior art seldom, however, teaches how the elastic bands may be applied to the product by continuous application of adhesive to the elastic ribbon, and yet having only the selective critical crotch portion of the elastic effectively operative. Among those patents which do are:

| U.S. Pat. No. | | | |
|---|---|---|---|
| | 4,331,501 | 82-05-25 | Teed |
| | 4,325,372 | 82-04-20 | Teed |
| | 4,309,236 | 82-01-05 | Teed |
| | 4,405,397 | 83-09-20 | Teed |
| | 4,353,762 | 82-10-12 | Bouda |
| | 4,261,782 | 81-04-14 | Teed |
| | 4,239,578 | 80-12-16 | Gore |
| | 3,984,272 | 76-10-05 | Teed |

OBJECTS OF THE INVENTION

One object of the present invention is to provide a method and apparatus for joining continuously-stretched bands of elastic in selected, spaced areas at pre-determined points along a continuously-moving, inelastic web.

A further object of the present invention is to provide a method and apparatus for deactivating certain portions of the adhesive-plus-elastic band at selected portions of the inelastic web.

Still a further object of the present invention is to provide a method and apparatus which applies adhesive in changing patterns and amounts so as to disassociate the stretched elastic strand from selected portions from the inelastic webs.

SUMMARY OF THE INVENTION

In the present invention, a disposable baby diaper or, in larger form, a disposable absorbent pad for an ambulatory incontinent adult, is manufactured in apparatus and by a process where a web of pervious top coverstock of selected shape is supplied to a similarly-designed impervious web of plastic-backing sheet. Between the two webs, a plurality of absorbent batts or pads are disposed, in spaced relation. Furthermore, in selected portions along the side edges of the webs, generally adjacent to the aforementioned batts, stretched elastic strands are secured to one or both of the webs, while in the stretched condition, by an adhesive which is continuously applied to the full length of the stretched elastic band. At selected areas of the elastic band, the adhesive is modified so that the adhesive secures the elastic strands to a web only in selected portions. Thus the web is separated from those portions of the elastic strand where the adhesive is modified, permitting elastic portions to snap back and become relaxed, and also permitting the elastic ribbon in the area attached to the web to contract or gather until the elastic ribbon in that area is relaxed.

With the above and other objects in view, further information and a better understanding of the present invention may be achieved by referring to the following detailed description:

DETAILED DESCRIPTION

For the purpose of illustrating the invention, there is shown in the accompanying drawings a form thereof which is at present preferred, although it is to be understood that the various instrumentalities of which the invention consists can be variously arranged and organized, and that the invention is not limited to the precise arrangement and organizations of the instrumentalities as herein shown and described.

In the drawings, wherein like reference characters indicate like parts:

FIG. 1 is a perspective view of a baby diaper made according to the present invention.

FIG. 2 is a top plan view of a baby diaper, with areas cut away to show the adhered and un-adhered portions of the elastic bands.

FIG. 3 is a simplified perspective view of a diaper assembly line, illustrating the absorbent pads, and the stretched elastic bands.

FIG. 4 is a partial vertical cross-sectional view of the adhesive applying mechanism.

FIG. 5 is a top illustration of one pattern of adhesive.

FIG. 6 shows a top view of a modified pattern of adhesive.

FIG. 7 is a vertical cross-sectional view of yet another modified pattern of adhesive.

U.S. Pat. Nos. 3,806,003 and 4,081,301, which are hereby incorporated herein by reference, disclose a form of disposable diaper and a method and apparatus for manufacturing one form thereof wherein the diaper has elastically-contractible flexible side portions. It is apparent, however, to those who are skilled in the art and have studied the aforementioned two patents, that the process and apparatus for making the product are extremely complicated because the adhesive for securing the stretched elastic ribbon to the inelastic web material must be either intermittently applied to the stretched, elastic ribbon; or, conversely, if use is made of an elastic ribbon having a heat-activatable adhesive coating on at least one side thereof, such adhesively coated ribbon must be intermittently activated to provide a product shown in the U.S. Pat. No. 3,860,003.

In my invention, the process and apparatus are substantially simplified because the adhesive can be continuously applied to the stretched elastic ribbon without the need for any selective activation of a ribbon containing heat-sensitive adhesive.

Referring now to FIG. 1, I have illustrated a baby diaper 5 which includes an absorbent body portions 6 and tape tabs 7, as well as a pair of elastic bands or strands 15.

Such a baby diaper is well known in the art and is generally considered to be a "shaped elastic-leg diaper" and many are sold in the market under the brand names of "Luvs" (Procter & Gamble), "Huggies" (Kimberly-Clark), and many under private-label brands and also as generic products.

Referring now to FIGS. 2 and 3, I have illustrated a continuous web 10 of inelastic material such as nonwoven coverstock, the kind well known in the construction of disposable baby diapers, sanitary napkins, and the like. This web 10 has portions (along the side thereof) removed, as at 11, to form a shaped or "hourglass" configuration. The wider ends 12 of the pads are, during the construction of the pad, connected to each other along the line 13, and it is only after the entire pad has been assembled that a suitable cutoff knife (not shown) separates the pad along the severing line 13.

Generally adjacent each of the narrow portions of the web, there is a batt or mat 14 of absorbent material which, in its preferred form, is a comminuted cellulose fluff-like material. However, it is to be understood that this batt 14 may be made of crepe wadding, absorbent tissue, hydrophylic foam or any similar absorbent material.

On each side of the web 10, between the batt 14 and the narrowed edge 11, I have secured a stretched elastic strand 15. This strand is applied to the web at the assembly station 16, in a stretched condition and in a manner clearly disclosed in U.S. Pat. No. 4,081,301.

In order to hold the elastic strand 15 in position, I apply a line of glue 17 to one side of the strand 15 by means of a well-known adhesive applicator 18.

It is preferred that the strip of adhesive 17 be quite narrow so as to be retained completely on the top of the elastic strand 15 without flowing over the sides of said strand.

In order to complete the assembly of the pad, I provide an impervious web 19. This impervious web 19 (which may be a polyethylene plastic sheet) overlies the previously described assembly of nonwoven web, elastic strand, batt and adhesive.

The adhesive extruder 18 lays down upon the adhesive band 15, the strip of adhesive 17 in a continuous fashion as is shown particularly in FIG. 3. However, the adhesive strip, though continuous, is not uniform in cross section or quantity, and the pattern of such strip may take many forms as is shown, by way of illustration, in FIGS. 5, 6 and 7.

In FIG. 5 the portion 20 of the adhesive 17 rests upon the elastic 15 in a wider band than does the portion 21. Thus both the cross section of the portion 20 and its amount of adhesive exceeds the cross section of the portion 21 and the amount of adhesive laid down in that area.

As is shown particularly in FIGS. 2 and 3, the lesser amount of adhesive is laid down upon the elastic in such a manner that it bridges the cutoff lines 13. The heavier amount of adhesive 20 is laid down upon the elastic 15 in the generally crotch portion of the diaper, in the area generally adjacent the cutout portions 11.

In FIG. 6 I illustrate how the continuous strip of adhesive may be modified so that the wider portions 22 become a continuous strip of dots or drips 23 in the portion of the assembly spanning the cutoff lines 13.

FIG. 7 illustrates how the amount of adhesive may be varied in a vertical direction. Thus the portions 24 are thicker than the portion 25, in a vertical direction.

Any one of the arrangements shown in FIGS. 5, 6 and 7 may be incorporated in the process, apparatus and product of the present invention.

I have found that in the construction of the diapers, it is desirable to have the elastic applied in a continuous manner so as to assure control of the manufacturing process. Moreover, it is desirable to have the adhesive applied continuously to the elastic so that at all stages of the assembly of elastic to the continuously-moving web, the parts remain in registry and under assembled control.

However, after the cutoff knives have severed the individual sections of the diapers along the line 13, it is also desirable to have the elasticating portions in the wider sections 12 of the diaper rendered less effective than the elasticating portions in the crotch portion 11.

Thus I apply the adhesive in the sections 21, 23 or 25 in such a manner that the retaining forces of adhesive on the elastic are less than the contracting forces of elastic itself, so that when the elastic bands 17 are severed along the lines 13, the force of contraction in the elastic bands is greater than the retaining force of the elastic in those portions and the ends of the rubber bands are rendered ineffective and unable to induce any contracting forces on the diaper.

This requires a careful balance of the amount of adhesive laid upon the elastic 15 by the nozzle 18, and under delicate control so that the amount of adhesive in the crotch portion 11 is sufficiently great to overcome any contracting forces in the elastic, and thus permit the elastic to gather or contract the assembled diaper in the crotch area. At the same time the careful application of a minimal amount of adhesive in the portions 21, 23 and 25 enable the elastic to be held in place against the pad during the manufacturing operation, but once the pads are severed one from another, the elastic and contractible forces in the rubber are greater than the holding forces of adhesive applied to the elastic in that area so that the ends of the rubber bands can "snap back" away from the assembled diaper pad and thus prevent the elastic from contracting the diaper in the waistband portions 12.

Thus it can be seen that I have provided a process and apparatus which enables a stretched elastic strand to be secured to a supporting web in such a manner that portions of said strand are free to "snap back" when the tension of the strand is released, and that all of this simplified procedure can be accomplished without the need for intermittent applications of adhesive or without the need for intermittent activation of an adhesively-coated elastic strand.

It is furthermore to be understood that my present invention may be embodied in other specific forms without departing from the spirit or special attributes; and it is, therefore, desired that the present embodiments be considered in all respects as illustrative and, therefore, not restrictive, reference being made to the appended claims rather than to the foregoing description to indicate the scope of the invention.

Having thus described my invention, what I claim as new and desire to protect by Letters Patent are the following:

1. A method for continuously attaching selected lengths of elastic ribbon to isolated portions of a moving, substantially inelastic web, of inter-connected articles to impart an elasticized character to pre-determined isolated portions of said articles, while preserving the substantially inelastic character of said articles and area where said ribbon is unattached to said web, said method comprising the steps of:
   feeding an elastic ribbon to an assembly station in a stretched condition,
   continuously applying an adhesive to said stretched elastic ribbon along the length of said ribbon while said stretched elastic ribbon is being fed to said assembly station,
   feeding a web of inter-connected articles made with webs of substantially inelastic material to said assembly station,
   reducing the quantity of adhesive applied to said stretched elastic ribbon between selected areas of said ribbon,
   adhering the stretched elastic strand to said inelastic material in said pre-determined areas,
   maintaining said elastic ribbon in a stretched condition at least until said adhesive sets up,
   the contracting force of elastic in the pre-determined area being less than the adhesive force between said elastic and said inelastic web in said pre-determined areas while the contracting force of the elastic between said pre-determined areas exceeds the adhesive force between the elastic and the inelastic material,
   cutting said elastic ribbon transversely in an area which is between said pre-determined areas thereby permitting contractible force in the elastic between said pre-determined areas to overcome the adhesive bond adjacent thereto and releasing said elastic between the pre-determined areas from the inelastic material and forming severed unadhered ends of elastic at both ends of each length of the stretched elastic ribbon which is adhered to said web in said pre-determined area, and
   allowing the severed unadhered ends of elastic ribbon to relax and contract to the unstretched state, whereby said unadhered ends to not impart an elasticized character to said web, nor do they interfere with the functioning of the elasticized portion of the web to which the selected lengths of elastic ribbon are adhered in the pre-determined areas.

2. A method of intermittently attaching an elastic ribbon to pre-determined, isolated portions of at least one of a pair of continuously moving, substantially inelastic, superimposed webs to impart an elasticized character thereto, while preserving the substantially inelastic character thereof in areas where said ribbon is unattached to said web, said method comprising the steps of:
   feeding an elastic ribbon to an assembly station in a stretched condition,
   continuously applying an adhesive on said stretched elastic ribbon, while said stretched elastic ribbon is being fed to said assembly station, and
   feeding said first and second webs of substantially inelastic material to said assembly station,
   maintaining said elastic ribbon in a stretched condition at least until said adhesive sets up,
   cutting said elastic ribbon transversely in an area which is adhered to said web, thereby forming severed, ends of elastic at both ends of each length of stretched, elastic ribbon adhered to said web,
   and allowing portions of the severed, ends of said elastic ribbon to relax and contract to their unstretched state, whereby said portions do not impart an elasticized character to said web, nor do they interfere with the functioning of the elasticized portion of the web to which the selected lengths of elastic ribbon are adhered.

3. The process of claim 1 wherein one of said inelastic webs is an impervious sheet and the other of said webs is a pervious sheet.

4. The process of claim 3 wherein the impervious sheet is polyethylene.

5. The process of claim 3 wherein the pervious web is a nonwoven coverstock material.

6. An apparatus for continuously attaching selected lengths of plastic ribbons to pre-determined isolated portions of a moving substantially inelastic web to impart an elasticized character thereto while preserving a substantially inelastic character of said web in areas where said ribbon is unattached to said web, said apparatus comprising:
   means for feeding an elastic ribbon to an assembly station in a stretched condition,
   means for continuously applying adhesive to said elastic ribbon at pre-determined intervals along the length of said ribbon while said stretched elastic ribbon is being fed to said assembly station,
   means for feeding a web of substantially inelastic material to said assembly station,
   means for applying variable amounts of the adhesive to the elastic ribbon as the elastic ribbon passes beneath the adhesive-applying means,
   means for insuring that the adhesive applied between the selected areas of the web have an adhesive force which is less than the contractible force of the stretched ribbon adjacent thereto,
   means for maintaining said elastic ribbon in a stretched condition at least until said adhesive sets up,
   means for cutting said elastic ribbon transversely in an area between said selective areas thereby permitting the elastic ribbon between the selected areas to overcome the adhesive force of the adhesive adjacent thereto, so that the elastic ribbon forms severed, unadhered ends of elastic at both ends of each of selected length of stretch elastic ribbon in said selected areas.

7. The apparatus of claim 6 wherein the means for cutting the elastic ribbon severs the web along the line passing through the adhesive which is disposed between the selected areas.

* * * * *